United States Patent [19]

Moriyama

[11] Patent Number: 4,791,945

[45] Date of Patent: * Dec. 20, 1988

[54] POWER OPERATED TOOTHBRUSH

[76] Inventor: Toshio Moriyama, 802-14, Higashi Koiso, Ohisomachi, Nakagun, Kanagawaken, Japan

[*] Notice: The portion of the term of this patent subsequent to Jul. 20, 2001 has been disclaimed.

[21] Appl. No.: 103,351

[22] Filed: Dec. 13, 1979

[51] Int. Cl.4 .............................................. A45D 44/18
[52] U.S. Cl. .................. 132/84 R; 15/22 R; 132/11 A
[58] Field of Search ............... 132/11 A, 11 R, 84 R; 15/22 R, 23

[56] References Cited

U.S. PATENT DOCUMENTS

| 2,486,062 | 10/1949 | Ridner, Sr. | 132/84 R |
| 2,850,753 | 9/1958 | Pelletier | 132/84 R |
| 2,883,692 | 4/1959 | Kaye et al. | 132/84 R X |
| 3,195,537 | 7/1965 | Blasi | 132/84 R X |
| 3,233,265 | 2/1966 | Hartmann | 15/22 R |
| 3,489,936 | 1/1970 | Boyles | 132/11 A |
| 3,546,501 | 12/1970 | Kircher | 15/22 R |

Primary Examiner—Richard J. Apley
Assistant Examiner—J. Welsh
Attorney, Agent, or Firm—Barnes, Kisselle, Raisch, Choate, Whittemore & Hulbert

[57] ABSTRACT

A power operated toothbrush including a brush supporting arm which is pivoted on two crank means. The distance between a crank shaft and a crank pin of one of the crank means is continuously changed so that the turning motion or oscillatory motion of a brush member which is mounted on an end of the brush supporting arm can be produced and one of the motions can be continuously changed to the other.

4 Claims, 3 Drawing Sheets

POWER OPERATED TOOTHBRUSH

BACKGROUND OF THE INVENTION

A method in which the brush portion is moved reciprocatively in parallel to the tooth row is most popularly adopted when teeth are brushed while operating a toothbrush by a hand. Also in case of power-operated toothbrushes, reciprocatory motions alone are performed by the brush and only the surface portion of the tooth row is brushed. Namely, the interior of the gingival groove between the tooth and gingiva, where dental dirts are readily deposited, is hardly cleaned.

As the result of researches, it was found that in order to remove dental dirts, food remains and other foreign substances from narrow dents such as gingival grooves, good results are obtained when top ends of hair of a toothbrush are inserted into the gingival grooves and the base portions of the hairs are turned with the top ends of the hairs being as fulcrum to impart to the top ends of the hairs such forces that the top ends of the hairs are caused to dig out foreign substances from the gingival grooves and spatter them out of the gingival grooves spirally, and it was also found that for removal of foreign substances such as mentioned above, which are stuffed between adjacent tooth neck surfaces, reciprocatory motions of the brush along these adjacent tooth neck surfaces are very effective.

BRIEF SUMMARY OF INVENTION

The present invention relates to a power operated toothbrush. More particularly, the present invention relates to a power operated toothbrush in which ideal motion for the toothbrush, that is, turning motion or oscillatory motion is produced. Motions of the brush member can be consecutively changed, for example, from turning motions to oscillatory reciprocatory motions or from oscillatory reciprocatory motions to turning portions, and that the turning loci of turning motions can be freely changed. Thus, in the toothbrush of the present invention, the motions of the brush member can be freely controlled according to the locales to be cleaned.

DETAILED DESCRIPTION OF THE INVENTION

One embodiment of the toothbrush of the present invention will now be described in detail with reference to the accompanying drawings.

Figure 1:
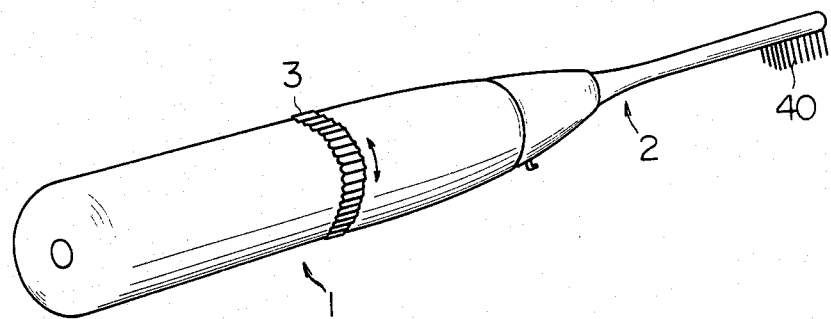
FIG. 1 is a perspective view illustrating the toothbrush of the present invention on the whole.

Referring to FIG. 1, in the toothbrush of the present invention, a brush member 2 is projected from a grip 1, and an annular switch 3 is mounted on the grip 1. A prime mover member for moving the brush member 2, such as a motor, a driving member and, if necessary, a battery are contained in the grip 1. These elementary members are illustrated in a perspective view of FIG. 2.

Figure 2:
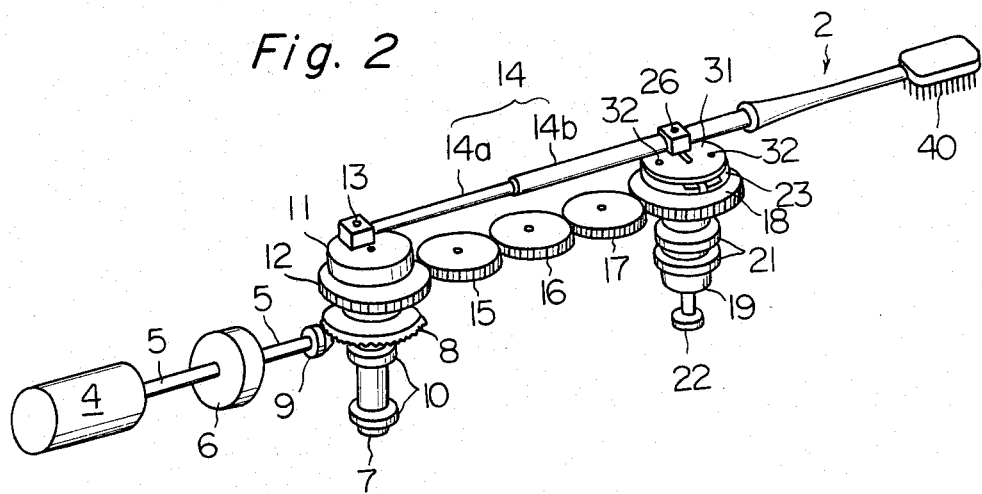
FIG. 2 is a perspective view showing a prime mover member, a driving member and a brush member in the toothbrush of the present invention.

Referring to FIG. 2, an output shaft 5 of a motor 4 has a reduction gear 6 in the midway thereof, and a bevel gear 9 engaged with a bevel 8 integrated with a main crank shaft 7 is mounted on the top end of the output shaft 5. The main crank shaft 7 is supported on a supporting member (not shown) through a bearing 10, and a main crank 11 and a spur gear 12 are fixed to the main crank shaft 7. A brush supporting arm 14 is pivoted on the main crank 11 through a main crank pin 13. In the embodiment illustrated in FIG. 2, the brush supporting arm 14 includes inner and outer two tubes 14a and 14b, which are slidably fitted, and the length of the supporting arm 14 can be changed by relative sliding movements of the inner and outer tubes 14a and 14b. The end of the tube 14a of the supporting arm 14 is stationarily pivoted on the main crank pin 13. The spur gear 12 constitutes a gear row acting as the driving member together with intermediate gears 15, 16 and 17 and spur gear 18. The spur gear 18 is integrally supported on a sub-crank shaft 19. Instead of the above-mentioned gear row, a chain or belt spread between the spur gears 12 and 18 may be used as the driving member. As illustrated in detail in FIG. 3, the sub-crank shaft 19 is supported on a supporting member 20 through a bearing 21, and a slide pin 22 is slidably inserted through the center of the sub-crank shaft 19 and a disc-shaped sub-crank 23 is integrally mounted on the top end of the slide pin 22. A T-shaped notch 24 is formed on the sub-crank 23 and a deep groove 25 is formed in the central portion, and a sliding piece 27 having a sub-crank pin 26 implanted thereon is slidably fitted in the T-shaped notch 24. Both the ends of a spring 28 are fixed in the T-shaped notch 24 and the spring 28 always urges the sub-crank pin 26 so that it is located at an eccentric position. A small hole 29 is formed on the sliding piece 27 and one end of an L-shaped lever 30 pivoted in the groove 25 is inserted in this small hole 29. The other end of the L-shaped lever 30 butts against the top of the slide pin 22 to urge the slide pin 22 downwardly. A cover 31 is fixed to the top of the sub-crank 23 by a screw 32 to prevent falling of the sliding piece 27. A long hole 33 is formed on the cover 31 so that the sliding movement of the sub-crank pin 26 is not disturbed by the cover 31. The tube 14b of the brush supporting arm 14 is pivoted and supported on the sub-crank pin 26. The end of the tube 14a of the brush supporting arm 14 is slidably inserted in the hollow interior of the cylindrical tube 14b.

Another embodiment of the brush supporting arm 14, though not illustrated in the drawings, will now be described.

Different from the telescopic supporting lever in the above embodiment, the brush supporting arm 14 of this embodiment is composed of one rod member which is not telescopic, and the central portion of the lever 14 is pivoted to the sub-crank pin 26 so that the lever 14 is kept stationary with respect to the pin 26. The end of the lever 14 is slidably pivoted on the main crank pin so that the brush supporting arm 14 is allowed to slide with respect to the main crank pin.

In the toothbrush of the present invention, the motor may be started by a battery or by a power supplied through an indoor wire. Furthermore, a charging type battery which can be charged by a power supplied through an indoor wire can be used. At any rate, normal rotation, reverse rotation and stopping of the motor 4 are performed by operating the switch 3.

The function of the toothbrush of the present invention will now be described.

Figure 3:
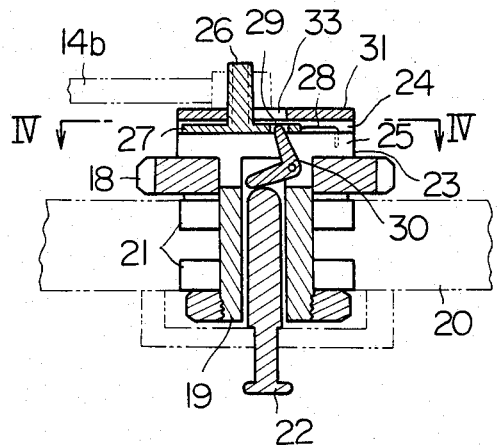
FIG. 3 is a side view showing the longitudinal section of a sub-crank shaft in the toothbrush of the present invention.
Figure 6:
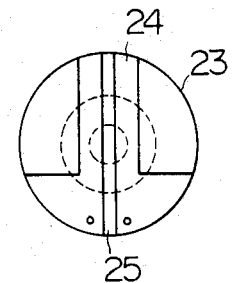
FIG. 6 is a top view of the sub-crank shaft shown in FIG. 5.
Figure 4:
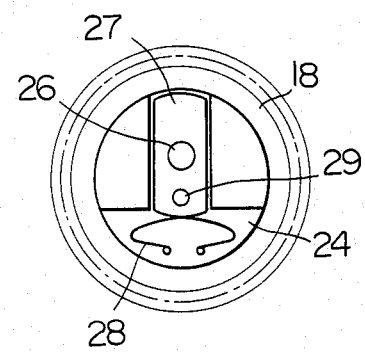
FIG. 4 is a view showing the state where a cover of a sub-crank is taken away.
Figure 5:
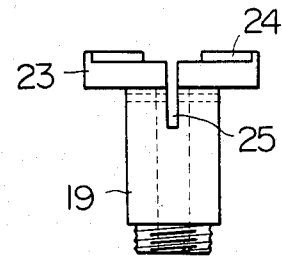
FIG. 5 is a front view showing a sub-crank shaft and sub-crank in the toothbrush of the present invention.
Figure 7:
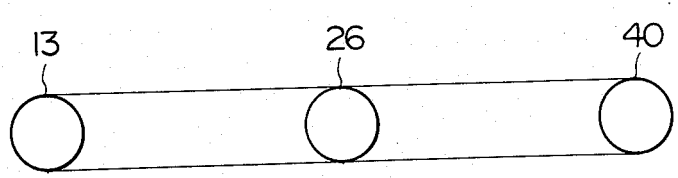
FIGS. 7 to 10 are diagrams illustrating loci of motions of hairs of the brush member in the toothbrush of the present invention.

When a hair 40 of the brush member 2 is caused to make a turning motion as shown in FIG. 7, the slide pin 22 is projected to the lowermost position. The slide pin 22 is always urged by the elastic force of the spring 23 through the sliding piece 27 and L-shaped lever 30 so that the slide pin 22 is downardly projected. In this state, as shown in FIG. 3, the sliding piece 27 is caused by the elastic force of the spring 28 to slide in the T-shaped notch 24 of the sub-crank 23 to the left end thereof. Accordingly, the sub-crank pin 26 is located on the left side of the center of the sub-crank shaft 19. In short, the pin 26 deviates from the center of the shaft 19 to the left. This deviation distance is made equal to the distance of deviation of the main crank pin 13 from the center of the main crank shaft 7. Furthermore, the main crank pin 13 and sub-crank pin 26 are arranged so that the line connecting the main crank pin 13 to the center of the main crank shaft 7 is in parallel to the line connecting the sub-crank pin 26 to the center of the sub-crank shaft 26. In this state, if the switch 3 is put on for normal rotation or reverse rotation, the motor 4 is rotated, and this rotation is transmitted to the main crank shaft 7 through the reduction gear 6, output shaft 5 and bevel gears 9 and 8 to rotate the main crank 11. Simultaneously, also the spur gear 12 is rotated by rotation of the main crank shaft 7, and the rotation of the spur gear 12 is transmitted to the sub-crank shaft 19 through the int intermediate gears 15, 16 and 17 and spur gear 18 to rotate the sub-crank 23. Since the tooth number of the spur gear 12 is the same as that of the spur gear 18 and the tooth number of the intermediate gear 15 is the same as those of the intermediate gears 16 and 17, the spur gears 12 and 18 are rotated in the same direction at the same speed. Accordingly, the main crank 11 and sub-crank 23 are rotated in the same direction at the same speed, and the brush member 2 is reciprocatively moved by the brush supporting arms 14a and 14b and the hair 40 of the brush member 2 makes a turning motion along an arc having the same radius as those of the main crank 13 and sub-crank 26.

In order to make the rotation of the brush member resemble the manual brushing movement, it is preferred that the rotation rate be 170 to 230 rotations per minute.

The above-mentioned turning motion is a circular motion. For some locales to be brushed, an oval motion is desired. In the present invention, the above-mentioned circular turning motion may be consecutively changed to an oval motion.

Figure 8:
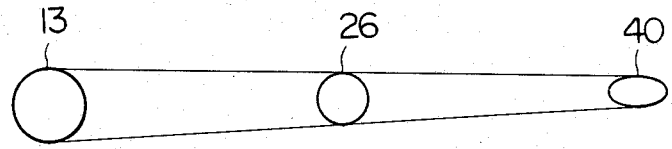

For this change of the mode of motions, the slide pin 22 is inwardly thrust appropriately against the elastic force irrespectively of whether the motor 4 is being rotated or is stopped, and the L-shaped lever 30 is turned in the clockwise direction in FIG. 3. Since the top end of the lever 30 is fitted in the small hole 29 of the sliding piece 27, the sliding piece 27 is shifted to the right and the sub-crank pin 26 is brought close to the center of the sub-crank shaft 19. In other words, the rotation radius of the sub-crank pin 26 is shortened. When the main crank 11 and sub-crank 23 are rotated in this state, since the angular velocity of the main crank is the same as that of the sub-crank 23, the distance between both the cranks is always changed. The quantity of this change is compensated gy changing the insertion quantity of the brush supporting arm 14a inserted in the brush supporting arm 14b. As the result, the hair 40 of the brush member 2 makes an oval motion as shownin FIG. 8. In the second embodiment not illustrated in the drawings, since the main crank pin 13 and brush supporting arm 14a are slidably pivoted, both the pin 13 and the arm 14a slide and the end of the arm 14a projects from the pin 13.

Figure 9:
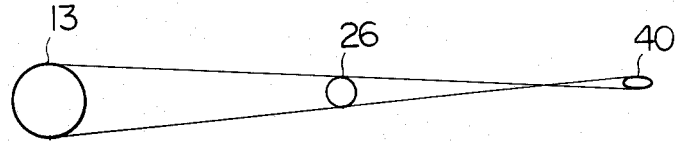
Figure 10:
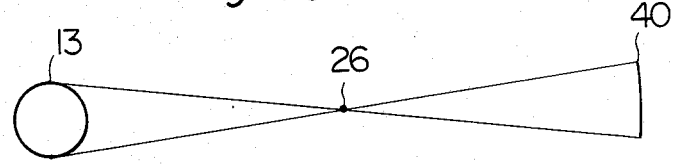

As the insertion quantity of the slide pin 22 is increased, the elliptical motion of the brush becomes small as shown in FIG. 9, and when the slide pin 22 is thrust most deeply, the center of the sub-crank pin 26 is made in agreement with the center of the sub-crank shaft 19. At this point, the main crank pin 13 makes a circular motion, and the brush supporting arm 14 and brush member 2 make oscillaory motions with the sub-crank pin 26 being as the fulcrum. Accordingly, the hair 40 of the brush member 2 is caused to make oscillatory reciprocary motions as shown in FIG. 10.

As will be apparent from the foregoing illustration, in the present invention, turning circular motions of the hair 40 can be changed to oscillatory motions merely by changing the thrust-in quantity of the slide pin 22 without stopping the motor.

In the power-operated toothbrush of the present invention, since turning circular motions can be changed to oscillatory reciprocary motions through intermediate oval motions in hairs of the brush member, the motions of the hairs can optionally be changed according to the positions of teeth to be brushed and motions optimal to these teeth can be selected. Furthermore, since this change of the motions can be accomplished consecutively without stopping the motor. Therefore, various brushing motions can be given to respective teeth and dental dirts and other foreign substances can be removed very effectively.

Furthermore, when teeth are cleaned by using the toothbrush of the present invention, since the brush is turned and rotated in the state where the tips of hairs are put and inserted in the gingival grooves, respective hairs move along a locus of an inverse conical shape. Accordingly, during the turning motions, dental dirts, food remains and other foreign substances in the gingival grooves are urged spirally and scraped out or driven away by the hair tips on which a largest force is imposed by such turning movement of hairs and the inherent elasticity of hairs, whereby dental dirts and other foreign substances in dents such as gingival grooves can be completely removed.

What is claimed is:

1. A power operated toothbrush including a handle having a motor therein, a toothbrush member including bristles on one end thereof, a pair of eccentric cranks positioned within said handle spaced longitudinally of the toothbrush member including portions secured to the toothbrush member at the spaced apart locations therealong and means for driving the eccentric cranks from the motor to impart at least one of a circular orbital motion and arcuate reciprocal motion to the toothbrush bristles, said drive means for the eccentric cranks including means for selectively varying the eccentricity of one of the cranks to selectively produce the circular orbital motion and arcuate reciprocal motion of the toothbrush bristles.

2. Structure as set forth in claim 1, and further including means for selectively varying the eccentricity of the one crank during movement of the toothbrush bristles.

3. A power operated toothbrush including a hollow casing, an electric motor within the casing, means for energizing the electric motor, a pair of cranks spaced apart longitudinally of the hollow casing having eccentric drive pins thereon, means for rotating the cranks the same amount and at the same speed from the electic motor including bevel gears secured to the motor and to one of the cranks, a spur gear on each of the cranks and a series of spur gears connecting the cranks to each other for simultaneous similar rotation, a toothbrush member having bristles on one end thereof, means for securing the other end of the toothbrush member to one of the cranks and means for securing the other of the cranks to the toothbrush member centrally thereof and means operably associated with at least one of the cranks for varying the eccenticity of the eccentric pin thereon to vary the motion of the bristles of the toothbrush between a complete circular orbital motion and a reciprocal arcuate motion.

4. Structure as set forth in claim 3, wherein the means for varying the eccentricity of one of the pins includes a sliding eccentric crank pin member, a spring pressed bell crank one end of which is positioned in the sliding eccentric crank pin member urging the sliding eccentric crank pin member into its most eccentric position and a slide pin engaged with the other end of the bell crank operable on axial movement to move the bell crank in opposition to the bias therefor to reduce the eccentricity of the eccentric crank pin member.

* * * * *

UNITED STATES PATENT AND TRADEMARK OFFICE
CERTIFICATE OF CORRECTION

PATENT NO. : 4,791,945
DATED : December 20, 1988
INVENTOR(S) : Toshio Moriyama

It is certified that error appears in the above-identified patent and that said Letters Patent is hereby corrected as shown below:

On the Title Page, [*] Notice: should read
--The portion of the term of this patent subsequent to July 20, 2002 has been disclaimed.--

Signed and Sealed this

Sixteenth Day of May, 1989

Attest:

DONALD J. QUIGG

*Attesting Officer*    *Commissioner of Patents and Trademarks*